United States Patent [19]

Flemer, III

[11] Plant 5,080

[45] Aug. 2, 1983

[54] ZELKOVA SERRATA TREE

[76] Inventor: William Flemer, III, P.O. Box 191, Princeton, N.J. 08540

[21] Appl. No.: 329,716

[22] Filed: Dec. 10, 1981

[51] Int. Cl.[3] ..... A01H 5/12

[52] U.S. Cl. ..... Plt./51

[58] Field of Search ..... Plt./51

*Primary Examiner*—Robert E. Bagwill

[57] ABSTRACT

A Zelkova serrata variety of larger size than Zelkova serrata "Village Green", U.S. Plant Pat. No. 2,337, having vase-shaped configuration, larger leaves of paler green, turning more orange than rusty red of "Village Green", in the fall, cold hardiness at temperatures to −16 degrees F., good foliar resistance to air borne pollutants and good drought resistance in heavy clay soil.

2 Drawing Figures

My present invention relates to a new and distinct variety of Zelkova tree, which I have chosen to designate as "Green Vase", recognized botanically as "Zelkova serrata", this particular variety having originated in a cultivated field of young Zelkova serrata seedlings which were grown from Korean seed furnished to me by the Institute of Forest Genetics in South Korea, the seeds not being of any known patented variety.

The tree hereof was particularly noticeable, because it was more than twice the size of sibling seedlings in the same and adjacent rows.

Further since the growth habit is narrowly upright, terminating as it does with a vase-shaped crown, it resembles the upright American Elm and is thus very distinctive likewise.

Asexual propagation carried on by me, at Princeton Nurseries in Plainsboro Township, Plainsboro, N.J., by budding in rows of adjacent trees, such as Zelkova serrata "Village Green", U.S. Plant Pat. No. 2,337, and Zelkova serrata "Fordam" an unpatented variety, and another unpatented, unnamed variety, has established that the characteristics so far described together with others to be described in detail hereafter, come true in generation after generation.

In fact the variety of my invention, grew more than double the height of other clones and of other understock trees in which the buds did not live.

There are several other improved characteristics of my invention "Green Vase" including improved hardiness in cold temperatures as compared to Japanese Zelkova for example, there being no injury to trunk or branches under conditions of winter temperatures as low as sixteen degrees below zero F.

A valuable aspect of improvement provided by my new variety is its good foliar resistance to air-borne pollutants encountered in large cities and good drought resistance in heavy clay soils.

In summary therefore my new variety evidences the following briefly stated unique combination of characteristics which are outstanding:

1. Substantially increased size as compared with other Zelkova serrata, such as "Village Green", U.S. Plant Pat. No. 2,337.

2. Narrow, upright growth habit terminating in vase-shaped crown.

3. More cold hardy resistance, being able to survive at temperatures as low as −16 degrees F. without injury to trunk or branches.

4. Good foliar resistance to air borne pollutants.

5. Good resistance to drought in heavy clay soils.

6. Larger, paler green leaves than "Village Green", U.S. Plant Pat. No. 2,337.

7. Distinctive, more orange fall color of leaves as compared to rusty-red of "Village Green" at a similar time.

In the accompanying drawing, one of the views discloses a row of typical trees of my new variety on the right, compared with a row of trees of the variety "Village Green" on the left. The other view shows a typical tree alone and particularly illustrates the vase-shaped or fountain shaped general appearance of the variety.

Since colors are not the most distinctive characteristics of my new variety, no color illustrations are used but where color references occur in the following detailed description they are made from comparison with the Nickerson Color Fan, published by Munsell Color Company, and where general color terms are used they will be those ordinarily applied in such cases.

Parentage: Seedling of Zelkova serrata from seeds supplied by Institute of Forest Genetics, South Korea.

Propagation: Maintains its distinguishing characteristics through succeeding generations when propagated by budding.

Locality where grown and observed: Township of Plainsboro, Plainsboro, N.J.

Tree: Large size; upright; vase-shaped; tall; hardy.

*Trunk.*—Slender; smooth.

*Branches.*—Slender; smooth. Color — 2.5 YR 3/3 Moderate reddish brown. Lenticels — Abundant; pale; narrow; 2 mm long.

Foliage:

*Leaves.*—Quantity abundant. Size — Length — Average 12 cm. Width — Average 6 cm. Shape — Cordate base, acuminate tip. Color — Upper surface 2.5 GY 4/3, moderate olive green. Lower surface 2.5 GY 5/5, moderate yellow green. Thick. Margin — Serrate; moderately revolute. Petiole — Short. Glands — None.

Flower buds: Not significant.

Flowers: Not significant.

Petalage: Not significant.

Fruits: Not significant.

I claim:

1. A new and distinct variety of Zelkova serrata tree, substantially as herein shown and described, characterized particularly as to novelty by the unique combination of narrowly upright growth, terminating in a vase-shaped crown, growing much taller than Zelkova serrata "Village Green", larger leaves of paler green than "Village Green", excellent cold hardiness, surviving at temperatures as low as −16 degrees F., without trunk or branch damage, good foliar resistance to air-borne pollutants, and good drought resistance even in heavy clay soils.

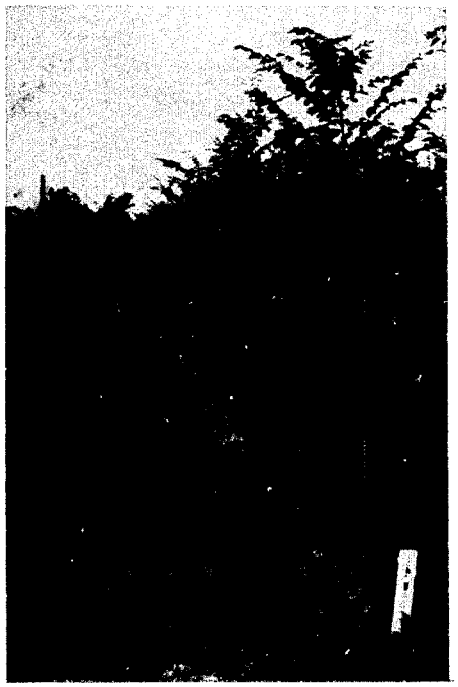
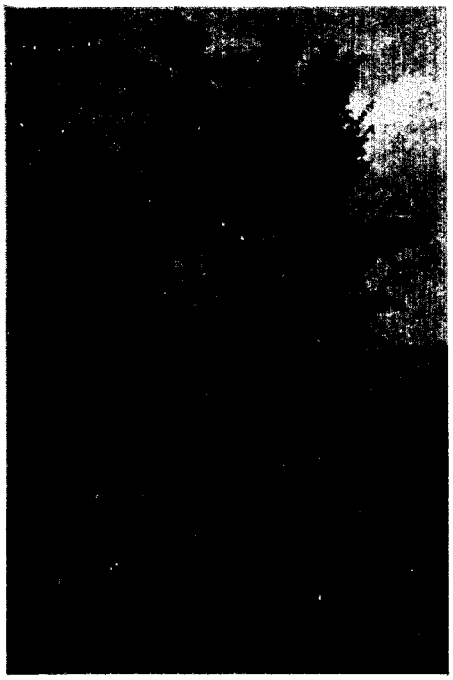

* * * * *